US005866694A

United States Patent [19]

Katinger et al.

[11] Patent Number: 5,866,694

[45] Date of Patent: Feb. 2, 1999

[54] PEPTIDES THAT INDUCE ANTIBODIES WHICH NEUTRALIZE GENETICALLY DIVERGENT HIV-1 ISOLATES

[75] Inventors: Hermann Katinger, Helligenstadterstr. 127 A/7/8, 1190 Vienna, Austria; Florian Ruker; Gottfried Himmler, both of Vienna, Austria; Thomas Muster, Graz, Austria; Alexandra Trkola, Vienna, Austria; Martin Purtscher, Vienna, Austria; Georg Maiwald, Vienna, Austria; Franz Steindl, Vienna, Austria

[73] Assignee: Hermann Katinger, Vienna, Austria

[21] Appl. No.: 843,718

[22] Filed: Apr. 17, 1997

Related U.S. Application Data

[62] Division of Ser. No. 361,479, Dec. 22, 1994, Pat. No. 5,693,752, which is a continuation of Ser. No. 932,787, Aug. 29, 1992, abandoned.

[30] Foreign Application Priority Data

May 14, 1992 [AT] Austria ..................................... 987/92

[51] Int. Cl.[6] ............................ C07H 21/02; C07K 1/00; C07K 14/00; A61K 39/21

[52] U.S. Cl. ......................... 536/23.1; 530/329; 530/328; 530/327; 530/325; 424/188.1; 424/184.1; 424/208.1; 424/204.1

[58] Field of Search .................................... 530/329, 328, 530/327, 324, 325; 424/184.1, 188.1, 204.1, 208.1; 536/23.1

[56] References Cited

FOREIGN PATENT DOCUMENTS 0362910 4/1990 European Pat. Off. .

*Primary Examiner*—Lynette F. Smith

*Attorney, Agent, or Firm*—Birch, Stewart, Kolasch & Birch, LLP

[57] ABSTRACT

This invention concerns peptides binding to antibodies which show neutralizing activity against different strains and clinical isolates of HIV-1 and which inhibit the fusion of cells infected with HIV-1. These peptides are combined with an adjuvant, as recombinant fusion proteins, chemically coupled to carrier molecules, as recombinant chimeric viruses or as recombinant antibodies.

18 Claims, 3 Drawing Sheets

Influenza/HIV inhibition of HIV-1 IIIB neutralization

PEPTIDES THAT INDUCE ANTIBODIES WHICH NEUTRALIZE GENETICALLY DIVERGENT HIV-1 ISOLATES

RELATED APPLICATIONS

This application is a divisional of Ser. No. 08/361,479 filed Dec. 22, 1994 now U.S. Pat. No. 5,693,752, which is a continuation of Ser. No. 07/932,787, filed Aug. 29, 1992, now abandoned.

FIELD OF THE INVENTION

This invention refers to peptides that induce antibodies which neutralize genetically divergent HIV-1 isolates. These peptides are applied with an adjuvant, as recombinant fusion proteins, chemically coupled to carrier molecules, as recombinant chimeric viruses or as recombinant antibodies. In addition, the stage of infection can be determined and the progression of the infection can be predicted with these peptides.

INTRODUCTION

Acquired immunodeficiency syndrome (AIDS) is the late stage clinical manifestation of long term persistent infection with human immunodeficiency virus type 1 (HIV-1). Immune responses directed against the virus and against virus-infected cells during the persistent infection usually fail to mediate resolution to the infection. Vaccines provide a possibility for eliciting an immune response that can prevent the establishment of a persistent infection or that can prevent the progression to AIDS. Most vaccine strategies against HIV-1 are directed against the surface glycoprotein gp160 which is made up of gp120 and gp41 and is responsible for virus binding to the cellular receptor CD4 and fusion activity.

However, in context with gp160 several phenomena that argue against the use of whole gp160 or gp120 as an immunogen have been observed. In vitro experiments showed that synergism between HIV-1 gp120 and gp120-specific antibodies block human T cell activation (1). This result supports the hypothesis that in vivo the humoral immune response against gp120 of HIV-1 suppresses T-cell activation and might be one reason for immunodeficiency. The proposed mechanism for this phenomenon is cross-linking and modulation of CD4 molecules through gp120 and anti-gp120. Experiments from Kion et al. (2) suggest that sequence homologies between gp160 and class II MHC molecules lead to immunodeficiency. In addition, a number of antigenic domains on gp160 are known to induce antibodies that enhance HIV-1 infection (3). Such effects known in context with gp160 could be avoided by using synthetic peptides or other subunit vaccines that only contain immunogenic and neutralizing epitopes as immunogens. Immunogenic peptides corresponding to parts of different viral proteins have already been used for successful immunization (4,5,6).

The use of synthetic peptides as immunogens offers a number of advantages. The antibodies produced have a predetermined specificity, and in the case of viruses, they can be selected to represent structures on the surface of virions. The synthetic polypeptides also are interesting in that they can induce antibody responses not seen under normal conditions. For example, it was found that in the hemagglutinin of influenza virus there are five major antigenic regions and that under conditions of natural infection the immune response includes antibodies only to these regions. With synthetic polypeptides, an immune response against other regions of the hemagglutinin polypeptide can be generated, and these antibodies have been found to be capable of neutralizing the virus. Therefore it is possible to induce neutralizing antibodies that have a broader reactivity than antibodies induced by whole proteins (4). In addition, immunizations with peptides derived from the nucleotide sequence of foot and mouth disease virus (FMDV) are described. In contrast to immunizations with the corresponding whole protein of FMDV, immunizations with these peptides lead to neutralizing antibodies which were also protective (5). Furthermore, a peptide containing part of the V3 loop of gp120 from the HIV-1 isolate HIV-1 IIIb was shown to induce a protective immune response against virus challenge with the same HIV-1 isolate (7,8).

Because synthetic peptides themselves have poor immunogenicity, they have to be coupled to molecules that provide an adjuvant effect such as tetanus toxoid or keyhole limpet hemocyanin (5). Another possibility is to clone small peptides as fusion peptides with glutathione S-transferase of *Schistosoma japonicum* (9,10). In addition, attenuated viruses such as vaccinia, polio Sabin type 1 or influenza NA/B-NS can be used as vectors for immunogens. Vaccinia virus is used frequently as a vector of foreign genes of multiple pathogens. For example rabbits inoculated with recombinant vaccinia virus obtaining sequences from hepatitis B surface antigen (HBsAg), herpes simplex virus glycoprotein D, and influenza virus hemagglutinin produced antibodies to all three foreign antigens (11). Furthermore, a chimeric polio virus that expressed an epitope from gp41 of HIV-1 induced neutralizing antibodies against gp41 in rabbits (12). Since recently it is also possible to change the genome of influenza virus by in vitro mutagenesis (13). By means of this technique, it was possible to engineer a stable attenuated influenza A virus (14). In addition, by using this technique it was also possible to construct an intertypic chimeric virus, in which a six amino acid loop contained in the antigenic site B of the hemagglutinin of an H1 subtype was replaced by the corresponding structures of subtypes H2 and H3 (15). An advantage of influenza virus in this context is the availability of many variants so that repeated vaccination may be possible. Furthermore, influenza virus induces strong secretory and cellular immune responses, which may be advantageous for an anti-HIV-1 vaccine approach. In addition, it is unlikely that influenza virus is associated with the development of malignancies. There is no DNA phase involved in the replication of influenza viruses, which excludes the possibility of chromosomal integration of viral influenza genes.

The use of antiidiotypic antibodies is another possibility to achieve a specific immune reaction. Antiidiotypic antibodies are antibodies that specifically recognize and bind the antigen binding site of another antibody. As the combining sites of antibodies can be structurally looked at as a mirror image of the epitope that is bound, an antiidiotypic antibody corresponds to the mirror image of this primary mirror image, which means that an antiidiotypic antibody displays the internal image of the epitope that is bound by the idiotypic antibody. Although one can not always expect to find complete identity between the structure or the amino acid sequence respectively of the antiidiotypic antibody with that of the epitope, one can however see effects in practice that allow the conclusion that there is a structural, sequential or functional similarity between antiidiotypic antibodies and the respective epitopes. The use of antiidiotypic antibodies as a vaccine was initially proposed by Nisonoff and Lamoyi (16). In the case of African Sleeping Disease, it was first shown that a protective immune response against the causative agents, Trypanosoma brucei rhodesiense, could be elicited in BALB/c mice by vaccinating the mice with antiidiotypic antibody (17). In the case of viral antigens, the formation of antiidiotypic antibodies to a neutralizing epitope on the hemagglutinin molecule of Reovirus Type III was investigated. These antiidiotypic antibodies recognized the cellular receptor of Reovirus-hemagglutinin on both, cytolytic T-cells and neuronal cells, and were able to induce in mice a humoral as well as a cellular immune response specific to Reovirus-hemagglutinin (18, 19, 20).

BRIEF DESCRIPTION OF THE DRAWINGS

FIG. 1: Western blots of fusion peptides. Recombinant proteins expressed *E. coli* were purified as described in example 1 and 100 ng of each fusion peptide was fractionated by sodium dodecyl sulfate polyacrylamide gel electrophoresis on a 20% polyacrylamide gel and electroblotted onto a nitrocellulose filter. The blots were blocked with 0.5% nonfat dried milk in phosphate-buffered saline containing 0.1% Tween for 1h at room temperature. After washing, blots were incubated with antibody 2F5 (500 ng/ml) for 1h at room temperature. After washing, blots were incubated for 1h at room temperature with anti-human IgG-alkaline-phosphate-conjugate. Blots were developed with 1M diethanolamine buffer (pH9.6) containing 350 ug/ml nitro-blue tetrazolium chloride and 350 ug/ml 5-bromo-4-chloro-3-indolyl-phosphate.

Cutoff=the mean value (4-fold) of a HIV-1 negative serum (1:40)+3 fold standard deviation. The donors of a sera numbers 20, 25, 29, 35, 41, 44, 46 have been HIV-1 positive for at least five years and are still asymptomatic.

Figure 2:
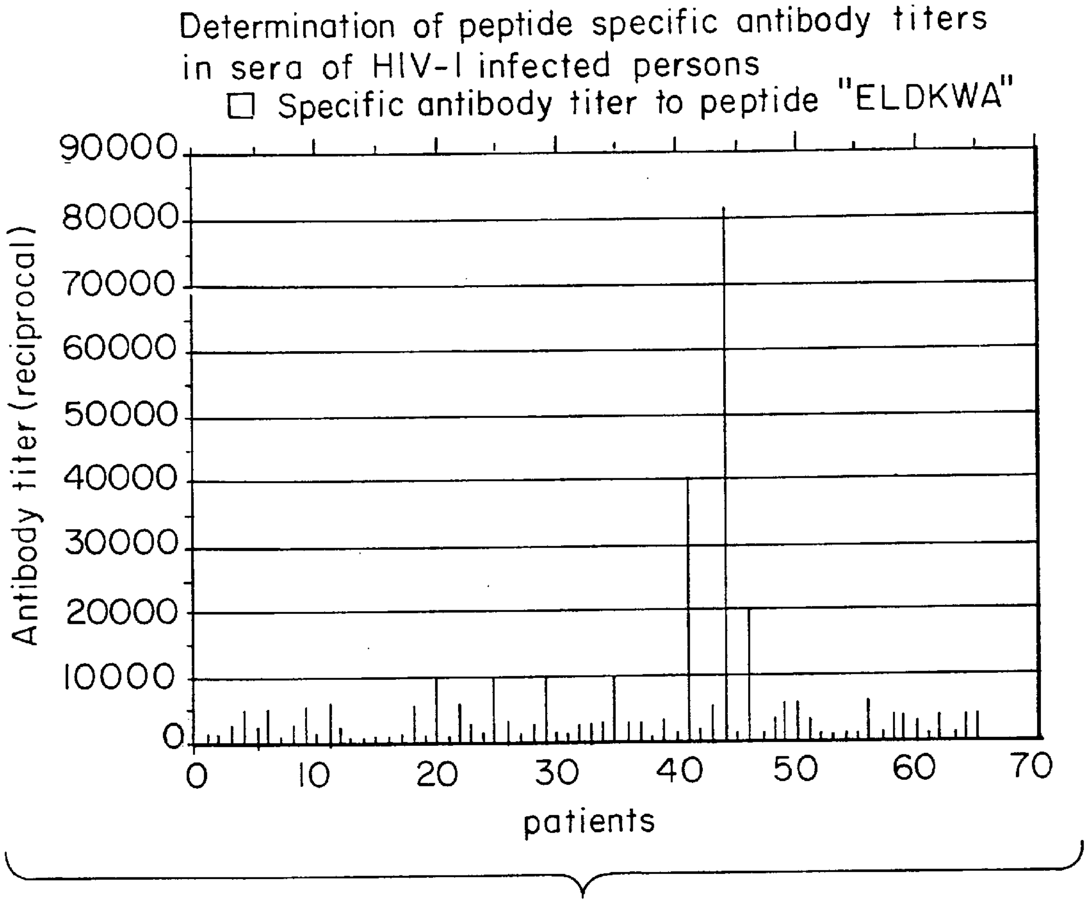

FIG. 2: Graphic of the specific antibody titres to the peptide with the amino acid sequence "ELDKWA" of 65 sera from HIV-1 positive donors.

Figure 3:
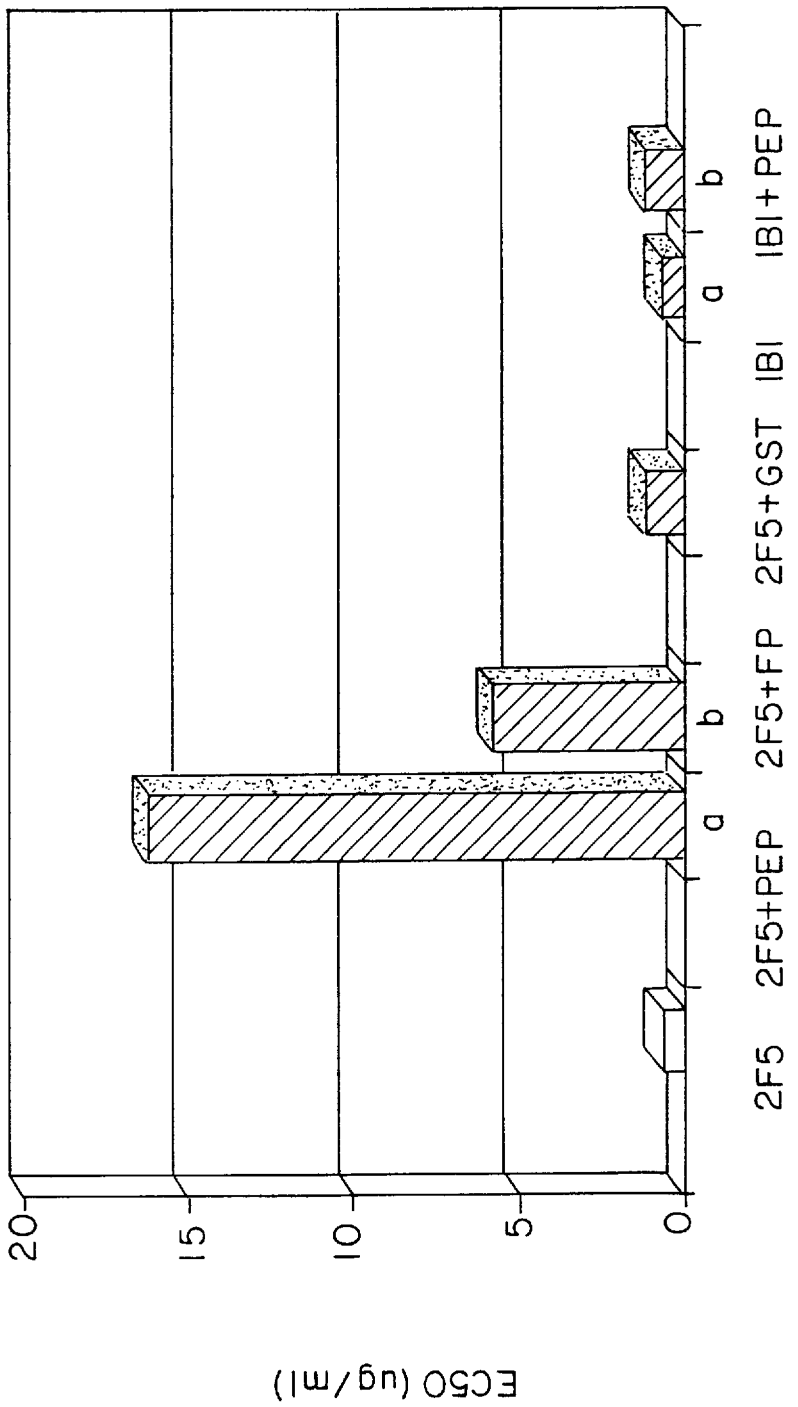

FIG. 3: Inhibition of neutralization by peptides. Synthetic peptide (PEP), fusion peptide (FP), and gluthathione-S-transferase (GST) were preincubated with humAb 2F5 or 1B1 for 1h at 37° C., and then a syncytia inhibition assay was performed. Antibodies were diluted in 2-fold steps starting with 5 μg/well. PEP, synthetic peptide ELDKWA (peptide corresponding to SEQ. ID. NO.: 1): a)25 μg, b) 5 μg/well; FP, fusion peptide ELDKWA with GST: a)25 μg, b) μg/well; GST; gluthathione-S-transferase: a)25 μg, b)5 μg per well; 1B1 neutralizing anti gp120 humAb.

DETAILED DESCRIPTION OF THE INVENTION

Figure 1A:
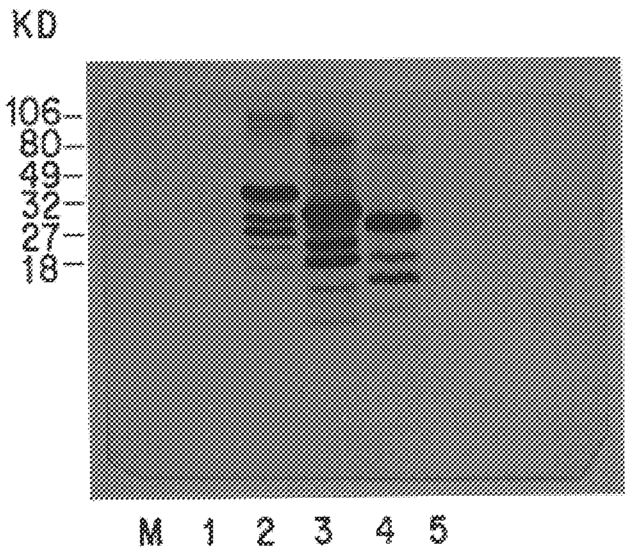
FIG. 1*a:* Lane 1, glutathione S-transferase (GST); lane 2, amino acids 597–677 of gp160 fused with GST; lane 3, amino acids 634–677 fused with GST; lane 4, amino acids 648–677 fused with GST; lane 5 amino acids 667–677 fused with GST.
Figure 1B:
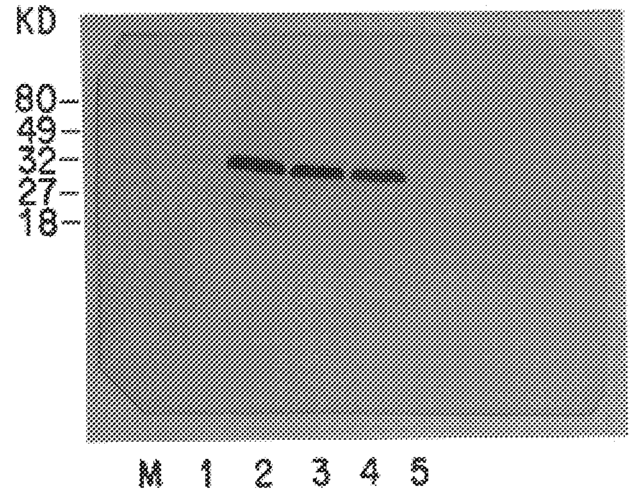
FIG. 1*b:* lane 1, GST; lane 2, GST fused with amino acids GLU LEU ASP LYS TP ALA (amino acids 662–667); lane 3, GST with amino acids LEU ASP LYS TRP ALA SER (amino acids 663–668); lane 4, GST with ASP LYS TRP ALA SER LEU (amino acids 664–669); lane 5, GST with amino acids LEU GLU LEU ASP LYS TRP (amino acids 661–666)
Figure 1C:
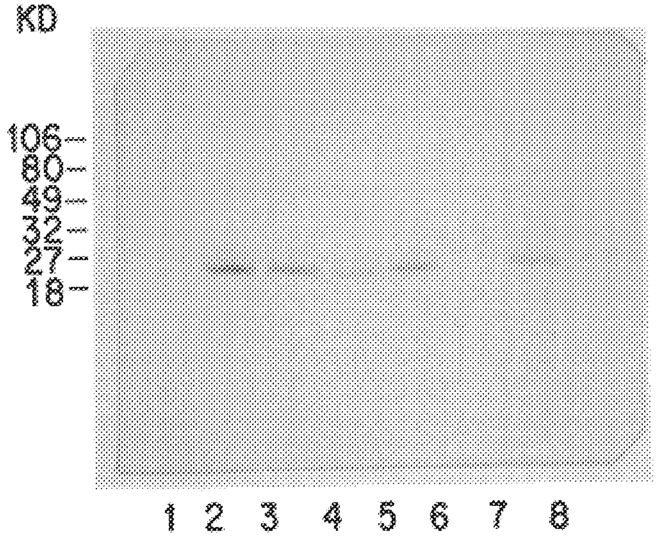
FIG. 1*c:* Fusion peptides with amino acid substitutions according to HIV-1 isolates with differences in the region of the 2F5 epitope. Amino acid differences are underlined. Lane 1, GST; lane 2, GLU LEU ASP LYS TRP ALA; lane 3, GLN LEU ASP LYS TRP ALA; lane 4 GLU LEU ASP LYS TRP ALA; lane 5, ALA LEU ASP LYS TRP ALA; lane 6, GLU LEU ASN LYS TRP ALA (reaction of this fusion peptide with the 2F5 antibody is not visible in this Western blot; however in ELISA competition assays this peptide was competitive with recombinant gp41 for binding to the 2F5 antibody); lane 7, GLU LEU ASP THR TRP ALA; lane 8, GLU LEU ASP LYS TRP ASP The antibody titres were determined by ELISA. The peptide was used in the form of a fusion peptide (in combination with glutathione-S-transferase). The fusion peptide was bound to 96-well microtitre plates 100 μl/well (2,5 μg/ml) and incubated overnight at 4° C. After washing three times with washing buffer HIV-1 positive sera were diluted $2^n$ fold (1:40–1:81920) in dilution buffer and aliquots were transferred to the test plate (100 μl/well) and incubated for 1h at RT. Then the plates were washed again three times with washing buffer. As a second antibody goat anti human Y-chain, conjugated with horseradish peroxidase, was used (diluted 1:1000, 100 μl/well). After 1h incubation at RT the plates were washed three times with washing buffer. Then the plates were stained using o-phenylene-diamine-dihydrochloride as substrate. The reaction was stopped with 2.5 $MH_2$ $SO_4$ and the plates were measured (measurement wavelength 492 nm, reference wavelength 620 nm) and evaluated.

Peptides comprising 6 amino acid residues (amino acids) that bind specifically to the monoclonal antibody 2F5 were used as immunogens to induce neutralizing antibodies against HIV-1. For identification of these peptides overlapping fragments of gp41 (HIV-1 isolate BH10) were cloned as fusion peptides with glutathione transferase. The different fusion peptides were obtained through hybridization of gp41 corresponding oligonucleotides which were cloned between the Bam HI and the Eco RI site of the plasmid pGEX-2T (Pharmacia). The recombinant plasmids were transformed into the *E. coli* strain DH5α and expression of the fusion proteins was induced with isopropylthiogalactoside (IPTG). The *E. coli* extract was then purified with glutathione-SEPHAROSE 4B columns, loaded on sodium dodecylsulfate-polyacrylamide gels, separated by electrophoresis and protein expression was analyzed by silver staining. Fusion peptides that were reactive with the monoclonal antibody 2F5 were identified by immunoblotting. Using this method peptides that bind to the monoclonal antibody 2F5 were identified. FIG. 1 shows Western blots of fusion peptides with overlapping fragments of gp160 of HIV-1 (isolate BH10). In contrast to constructs that comprise amino acids a 597 to 677, 634 to 677 and 648 to 677 (the numbering of amino acid residues corresponds to gp160 of HIV-1 isolate BH10, as described in the Swissprot database entry ENV$HIV10) which were reactive with the antibody 2F5, a fusion peptide comprising amino acids 667 to 677 did not show a positive reaction. This was the first indication that the epitope of the monoclonal antibody 2F5 is formed by amino acids within the sequence from position 648 to 667 of gp160. Based on these results, overlapping 6-mer peptides of this region were fused with the glutathione S-transferase. As shown in FIG. 1*b* the peptide containing the amino acid sequence GLU LEU ASP LYS TRP ALA (amino acids 662–667) was highly reactive with the antibody 2F5 whereas for peptides containing the amino acid sequence LEU ASP LYS TRP ALA SER (amino acids 663–668) or ASP LYS TRP ALA SER LEU (amino acids 664–669) reactivity with the monoclonal antibody was significantly lower. A peptide containing amino acid sequence LEU GLU LEU ASP LYS TRP (amino acids 661–666) showed no reactivity at all. These data suggest that the epitope of the monoclonal antibody comprises the amino acid sequence GLU LEU ASP LYS TRP ALA (SEQ. ID. NO.1) that corresponds to amino acids 662–667 on gp160 of the HIV-1 BH10 isolate. In this context both a synthetic peptide corresponding to this epitope sequence and a fusion protein containing this sequence were able to inhibit neutralization mediated by the 2F5 antibody (FIG. 3). Sequence comparison of that region revealed that the corresponding amino acid sequence is highly conserved between otherwise genetically highly divergent HIV-1 isolates (Table 2). We also were able to show that fusion peptides with amino acid substitutions—according to different HIV-1 isolates—in this region were also reactive with the 2F5 antibody (FIG. 1*c*).

The presence of antigenic domains around this region has been reported previously (21,22). Teeuwsen et al. reported a monoclonal antibody that reacted with a peptide corresponding to amino acids 643 to 692 of gp160. In addition Broliden et al. reported that HIV-1 antibody-positive human sera were reactive with a peptide corresponding to region 657–671. However, in both cases a specific epitope was not identified. The monoclonal antibody reported by Teeuwsen et al. had no neutralizing activity. Also the sera reactive with the peptide 657–671 of Broliden et al. showed just partial neutralizing activity. In different neutralization assays this group was able to show neutralizing activity against HIV-1 isolate IIIB but not against SF2 and RF. In contrast to this result, the monoclonal antibody 2F5 neutralizes a variety of different HIV-1 isolates including SF2 and RF (Table 1). These data suggest that the antibodies of the sera reported by Broliden et al. as well as the monoclonal antibody reported by Teeuwsen et al. have a different specificity and recognize a different epitope than the antibody 2F5.

The application of the peptides described in the present invention as of immunogen has several advantages. They comprise just 6 amino acids. Thus, other gp160 peptide sequences which induce antibodies that enhance HIV-1 infection or lead to immunosuppression can be avoided (2,3). Furthermore an effective HIV-1 vaccine should induce an immune response against HIV-1 isolates that vary considerably in their genomic sequences. In this context sequence comparison in the region of the 2F5 epitope revealed that the epitope of the 2F5 antibody is highly conserved between different HIV-1 isolates (Table 2). Since peptides with amino acid substitutions—corresponding to genetically different HIV-1 isolates—were reactive with the 2F5 antibody (FIG. 1*c*), it is likely that antibodies induced by peptides described in the present invention are directed against a variety of divergent HIV-1 isolates. In addition, the 2F5 antibody showed neutralizing activity against a wide variety of genetically different HIV-1 isolates which proves that peptides described in the present invention are presented as neutralizing epitopes (Table 1).

In order to know which variations of the epitope sequence are binding to the monoclonal antibody 2F5 we undertook a peptide mapping with a random hexapeptide library displayed on protein III of a filamentous phage (22a). The hexapeptide sequences of the eluted phage particles were compiled (Table 4).

There is a wide range of variation in the progression of HIV-1 related disease in different HIV-1 infected persons. In many cases HIV-1 infection ends up in AIDS-related complex (ARC) and AIDS within some years, while some HIV-1 positive persons remain asymptomatic. It has been shown that antibody titers against certain peptide epitopes are much lower in AIDS-patients compared to asymptomatic states (23). We found a significant correlation between the antibody titers to the peptides described in the present invention and HIV-1 related disease progression (FIG. 2). Patients number 20,25,29,35,41,44 and 46 who have a high antibody titer to peptides described in this invention (FIG. 2), did not show any progression in disease within the last five years so far. This means that generation of antibodies induced by peptides described in the present invention can inhibit or at least reduce the progression of HIV-1 related disease. The fact that there are rarely high antibody titers to peptides described in this invention found in sera of HIV-1 positive patients indicates that these epitopes on gp160 are not recognized readily by the human immune system, resulting in low HIV-1 neutralizing antibody titers specific to these epitopes. An objective of the present invention is also to present the peptides described in the invention in a proper form and to induce a sufficient neutralizing immune response.

EXAMPLE 1

The cloning and expression of peptides described in the invention as fusion proteins with glutathione S-transferase (GST) and immunizations of mice with these peptides is described. All cloning methods were done according to standard procedures (24). Oligonucleotides corresponding to the peptides described in the invention were hybridized and cloned between the Bam HI and Eco RI site of the plasmid pGEX-2T (Pharmacia). By this the $NH_2$-terminal ends of these peptides were fused with the COOH-terminal end of the GST. In addition, a stop codon was added to the COOH-terminal ends of the gp41 peptide sequences. These constructs were transformed into *E. coli* DH5α and expression of the fusion proteins was induced with isopropylthiogalactoside (IPTG). After three hours of induction bacteria were harvested by centrifugation, suspended in phosphate buffered saline (PBS, pH 7.2) containing 1% Triton-X-100 and sonicated. Bacterial debris was spun down by centrifugation and the supernatant was loaded on glutathione-SEPHAROSE 4B columns (Pharmacia). Elution of the fusion proteins was done with 20 mM glutathione and 120 mM NaCl in 100 mM Tris HCl (pH 8.0). Purified fusion proteins obtained by this procedure were used for immunizing mice according to standard procedures. As a control, mice were immunized with GST prepared in the same way as the fusion proteins. Sera from mice taken one week after the last immunization showed high neutralizing titers against peptides described in the invention and inhibited HIV-1 replication in vitro (Tables 6 and 7).

EXAMPLE 2

Example 2 describes the expression of peptide sequences described in the invention as part of the hemagglutinin of influenza A virus. In vitro mutagenesis was used to introduce this peptide sequence into the antigenic sites A,B,C,D and E of the hemagglutinin of influenza A virus (26, 27). These chimeric DNA-constructs were then "RNP-transfected" into influenza HK/WSN virus (13). These chimeric influenza/HIV viruses had the antigenic properties of said peptide. In antibody adsorption experiments these chimeric viruses inhibited HIV-1 neutralization by the antibody 2F5 (Table 5). Antisera of mice immunized with the chimeric viruses were reactive with said peptides (Table 6). Furthermore, in vitro these antisera neutralized different HIV-1 isolates (Table 7).

EXAMPLE 3

Example 3 describes the expression of peptides described in the invention as part of a so called "immunological supermolecule" in which the peptide sequence is inserted into the linker which connects the variable regions of the heavy and light chain of an immunoglobulin molecule. Specifically a single chain Fv construct of a neutralizing anti-HIV-gp120 antibody was made according to standard procedures (27). In this construct peptide sequences described in the invention were inserted into the linker which connects the variable region of the light chain with the variable region of the heavy chain. This recombinant protein was expressed in *E. coli* and purified according to standard procedures. Two functions were observed with this construct. First this construct showed the antigen binding properties of the original antibody and in addition this construct induced, when injected into mice, antibodies that neutralized different HIV-1 isolates (Table 7).

This "immunological supermolecule" provides the possibility to obtain an active and passive immunization at the same time. Basically, in such a construct the antigen binding neutralizing properties of an antibody and the presentation of a neutralizing epitope are combined. In persons already infected with HIV-1 the progression of infection could be slowed down with the first application by the antigen binding neutralizing properties, before the effective onset of the immune system is triggered by the neutralizing epitopes of this molecule. Thus the "time lag" usually observed between immunization and effective immune response of a typical active immunization could be overcome. In addition, it is most likely that during neutralization of already present HIV-1 virions the presentation of the epitope is very efficient.

EXAMPLE 4

Example 4 describes the formation of antiidiotypic antibodies to antibody 2F5 as well as the production of an antiidiotypic antibody by means of in vitro recombination techniques. Antibody 2F5 was used to immunize mice in order to induce the formation of antiidiotypic antibody. The immunization scheme used was according to standard procedures in order to enhance the frequency at which antiidiotypic antibodies are developed in the animal. The polyclonal sera so obtained were tested for their immunoreactivity, whereby it was determined by means of antigen-competition ELISA that a part of the humoral immune response was indeed directed against the combining site of the antibody 2F5. Thus it was proven that in those sera antiidiotypic antibodies were present. In order to test the concept of vaccination by means of antiidiotypic antibodies, the sera containing antiidiotypic antibodies where subsequently used to immunize another group of mice. After completion of this immunization procedure, it was possible to detect an immune response to the antiidiotypic sera that was qualitatively comparable to the above described immune reaction against the HIV-1 peptide part of the glutathione-S-transferase fusion protein described in example 1.

Since it was now proven that the described peptide has the quality necessary to act as an immunogen, and since furthermore it had been shown that by using antiidiotypic antibodies having the internal image quality of the described peptide it was possible to induce a HIV-1 neutralizing immune response, an antiidiotypic antibody was constructed by means of in vitro recombination techniques. In order to achieve this goal, one or more hypervariable regions (or parts thereof) of an existing, molecularly cloned antibody were substituted by peptide sequences described in the invention. The respective constructs where expressed as single chain Fv fragments in *E. coli,* and the recombinant proteins where purified according to standard methods. An HIV-1 neutralizing immune response was obtained by immunization of mice with the antiidiotypic proteins so produced lead to a HIV-1 (Table 7).

EXAMPLE 5

Example 5 describes the peptide mapping with a random hexapeptide library and immunizations of mice with phages containing peptides according to SEQ ID NO: 10 through SEQ ID NO: 25. The monoclonal antibody 2F5 was coated onto polystyrol tubes (Maxiscorp, Nunc, Denmark) at a concentration of 5 μg/ml in coating buffer (0.1M Na-Carbonate buffer, pH 9.6) overnight at 4° C. After washing with PBS, the surface was blocked with PBS containing 5% w/v skimmed milk powder at 36° C. for 2 hours. Washing with PBS was followed by incubation of a hexapeptide phage display library ($10^{11}$ transduction units in TPBS (PBS including 0.5% v/v Tween 20) overnight at 5° C. Extensive washing with TPBS was followed by elution of phage with elution buffer (0.1N HCl/Glycine pH 2.2, 1 mg BSA/ml). The eluate is neutralized with 1M Tris and used for infection of *E. coli* K91Kan. Phage is prepared from the infected culture by the methods described (22a). The procedure is repeated 3 times. The final eluate was used to produce transduced *E. coli* K91Kan. DNA of these clones was sequenced and the respective phage displayed hexapeptide sequence was derived by computer translation.

Clones with the SEQ ID NOs:10 through 25 (Table 3) were used for phage preparation and the respective phages were injected into mice. After two booster injections the respective sera were tested for HIV-1 neutralizing activity. All of these sera were neutralizing in vitro. The control serum was produced by immunization with wild-type phage f1 and did not neutralize HIV-1. In addition, oligonucleotides coding for SEQ ID NOs: 10 through 25 were introduced into gene VIII of fd-tet between amino acids 27 and 28 of the immature protein VIII by standard cloning techniques. The recombinant phages were produced in *E. coli* K91Kan, purified by standard techniques (PEG mediated precipitation followed by CsCl gradient centrifugation) and used as immunogen. The respective sera were found to be neutralizing in HIV-1 neutralizing assays whereas anti-wild type fd-tet was not.

TABLE 1

In vitro neutralization assays:

| | Isolate | | | | | |
|---|---|---|---|---|---|---|
| | IIIB | MN | RF | SF2 | A | C |
| number of positive tests | 8/8 | 2/2 | 2/2 | n.t. | 8/8 | 4/4 |
| neutralizing concentration (Ig/ml) | 10 | 10 | 10 | | 50 | 10 |

Table 1: Neutralizing properties of human monoclonal antibody 2F5

In vitro neutralization assay: Different concentrations of the 2F5 antibody were incubated with cell free virus preparations ($10^2$–$10^3$ $TCID_{50}$) 1 h at 37° C. Aliquots of $10^5$ H9 cells were added to virus/antibody mixtures and incubated for an additional hour at 37° C. After 20 days p24 antigen concentration as indicator for virus replication was determined from supernatants according to standard procedures.

TABLE 2

| | syncitia inhibition assay: | | | | | |
|---|---|---|---|---|---|---|
| | Isolate | | | | | |
| | IIIB | MN | RF | SF2 | A | C |
| number of positive tests | 18/18 | 11/11 | 6/10 | 1/1 | 1/1 | 2/3 |
| $EC_{50}$ (Ig/ml) | 12,8 | 12 | 13,7 | 1,9 | 27 | 10 |

Table 2: Syncytia inhibition assay: Antibody/virus mixtures were prepared as described in Table 1. To these mixtures $10^5$ AA2 cells were added and incubated at 37° C. After 5 days syncitia formation as indicator for HIV-1 replication was evaluated. Abbreviations: A and C are clinical isolates from Vienna.

TABLE 3

| | | | | | | |
|---|---|---|---|---|---|---|
| E | L | D | K | W | A | 43 |
| A | : | : | : | : | : | 5 |
| : | : | N: | : | : | : | 1 |
| : | : | : | : | : | D | 2 |
| A | : | : | T | : | : | 3 |
| Q | : | : | : | : | : | 2 |
| : | : | : | : | : | : | 1 |
| G | : | : | : | : | : | 1 |
| K | : | : | E | : | : | 1 |

Table 3: Peptide sequences bound by antibody 2F5:

Sequences present on gp160 of different HIV-1 isolates (SEQ. ID. NOs.: 1,4,2,3,8,6,7,5 and 9, respectively.) The number on the right side of each sequence indicates the number of incidences in the databases that were screened (SwissProt and GenPept).

TABLE 4

| | | | | | |
|---|---|---|---|---|---|
| S | : | : | : | : | : |
| G | R | : | : | : | : |
| G | A | : | : | : | : |
| A | H | E | : | : | : |
| A | C | : | Q | : | : |
| G | A | : | : | : | G |
| G | A | : | : | : | N |
| G | A | : | : | : | C |
| G | A | : | : | : | V |
| G | A | : | : | : | H |
| G | A | : | : | : | H |
| G | A | : | : | : | Q |
| A | Y | : | : | : | S |
| A | F | : | : | : | V |
| G | P | : | : | : | G |
| A | R | : | : | : | A |

Table 4:

Binding sequences found by screening a random hexapeptide library expressed on the surface of filamentous phage (sequences already described in Table 3 are not included) (SEQ. ID. Nos.: 10,11,12,13,14,15,16,17,18,19,20,21,22,23, 24 and 25, respectively.)

TABLE 5

| Influenza/HIV inhibition of HIV-1 IIB neutralization | | | |
|---|---|---|---|
| monoclonal antibodies: | residual IIB neutralization titer in % after incubation with: | | |
| | Mock | Influenza WSN | Influenza/HIV |
| 2F5 | 100% | 100% | 10% |
| 2G12 | 100% | 100% | 100% |

Table 5: Influenza/HIV inhibition of HIV-1 neutralization. Results are expressed as the reciprocal of the serum dilution giving >90% reduction in HIV titer following preincubation of the mABs 2F5 and 2G12 with culture medium (Mock), influenza WSN or influenza/HIV. 2F5 is the monoclonal antibody specific for the different epitope on gp160. Residual HIV-neutralizing activity was determined by incubating dilutions of the antibody/virus mixture with $10^3$ infectious units ($TCID_{50}$) of HIV-1 IIIb for 1h at 37° C. Aliquots (100 $\mu$l) of medium containing $10^4$ C8166 cells were added and the presence of syncytia was recorded after 48h as an indication of HIV infection.

TABLE 6

| Immunogen | Antibody titer: |
|---|---|
| K1 | <10 |
| K2 | <10 |
| K3 | <10 |
| F1 | 1600 |
| F2 | 6400 |
| F3 | 800 |
| SM1 | 3200 |
| SM2 | 400 |
| SM3 | 800 |
| V1 | 3200 |
| V2 | 3200 |
| V3 | 6400 |
| rA1 | <10 |
| rA2 | 400 |
| rA3 | 800 |

Table 6: Antibody titer. Three Balb/c mice each were immunized with either 100 $\mu$g GST (K), 100 $\mu$g Fusion protein (F), 100 $\mu$g of the "immunological supermolecule", 100 $\mu$g of the recombinant antiidiotypic antibody (rA) or 4.0 $\log_{10}$ $TCID_{50}$ of the recombinant influenza/HIV virus (V) and was boosted after 2 and 4 weeks. One week after the last immunization ELISA antibody was determined. Results are given as reciprocal values that gave significant positive values. The cutoff was the double value of a normal mouse serum. Recombinant gp41 was used as an antigen.

TABLE 7

| | Reciprocal neutralization titers of HIV-1 isolates Antiserum | | |
|---|---|---|---|
| | IIIB | RF | MN |
| P1 | 40 | 40 | 40 |
| P2 | 80 | 40 | 40 |
| P3 | 40 | 20 | 20 |
| V1 | 40 | 80 | 40 |
| V2 | 20 | 40 | <10 |
| V3 | 160 | 80 | 80 |
| SM1 | 20 | 40 | 40 |
| SM2 | 40 | 80 | 80 |
| SM3 | <10 | <10 | <10 |

TABLE 7-continued

| Reciprocal neutralization titers of HIV-1 isolates Antiserum | | | |
|---|---|---|---|
| | IIIB | RF | MN |
| rA1 | 40 | 40 | 40 |
| rA2 | 40 | 80 | 20 |
| rA3 | 80 | 40 | 40 |

Table 7: Neutralization of HIV-1 infection. Neutralization titers were determined by incubating 10 $\mu$l of heat inactivated antiserum with 40 $\mu$l virus supernatant containing $10^3$ infectious units of HIV-1 at 37° C. for 1h. Residual HIV-1 infectivity was measured as described in Table 5. Abbreviations: P . . . fusion peptide, V . . . chimeric influenza/HIV virus, SM . . . "immunological supermolecule". RA . . . recombinant antibody. Reciprocal neutralization titers of all controls were lower than 10.

Literature

1. Mittler, R. S., and K. Hoffmann. 1989. Synergism between HIV GP120 and gp 120-specific antibody in blocking human T cell activation, Science 245: 1380–1382

2. Zion, T. A., and G. W. Hoffmann. 1991. Anti-HIV and anti-anti-MHC antibodies in alloimmune and autoimmune mice, Science 253: 1138–1140

3. Jiang S., K. Lin and A. R. Neurath. 1991. Enhancment of human immunodefeciency virus type 1 infection by antisera to peptides from the envelope glycoproteins gp120/gp41, J.Exp.Med. USA 174: 1557–1563

4. Green, N., H. Alexander, A. Olson, S. Alader, T. M. Shinnckf, J, G. Sutciffle, and R. A. Lerner. 1982. Immunogenic Structure of the Influenza Virus Hemagglutinin, Cell 28: 477–487

5. Bittle, J. L., R. A. Houghten, H. Alexander, T. M. Shinnick, J. G. Sutciffle and R. A. Lerner. 1982. Protection against Foot-and-mouth disease by immunization with a chemically synthesized peptide predicted from the viral nucleotide sequence, Nature 298: 30–33

6. R. A. Lerner. 1982. Tapping the immunological repertoire to produce antibodies of predetermined specificity, Nature 299: 592–596

7. Wahren, B., G. Bratt, J. Hinkula, G. Gilljam, S. Nordlund, P. A. Broliden, L. Akerblom, B. Morein, and E. Sandström.1990. Monoclonal antibodies given as passive treatment to HIV-infected individuals, Cinguieme Collogue des Cent Gardes:263–268

8. Emini, E. A., W. A. Schleif, J. H. Nunberg, A. J. Conley, Y. Eda, S. Tokiycshi, S. D. Putney, S. Matsushita, K. E. Cobb, C. M. Jett, J. W. Eichberg, and K. K. Murthy. 1992. Prevention of HIV-1 infection in chimpanzees by gp 120 V3 domain-specific monoclonal antibody, Nature 355: 728–730

9. Fikrig E., S. W. Barthold, F. S. Kantor, and R. A. Flavell, 1990. Protection of mice against the lyme disease agent by immunizing with recombinant OspA, Science 250: 553–556

10. Johnson K. S., G. B. L. Harrison, M. W. Lightowlers, K. L. O'Hoy, W. G. Cougle, R. P. Dempster, S. B. Lawrence, J. G. Vinton, D. D. Heath, and M. D. Rickard. 1989. Vaccination against ovine cysticercosia using a defined recombinant antigen, Nature 338: 585–587.

11. Perkus, M. E., A. Piccini, R. R. Lipinskas, and E. Paoletti. 1985. Recombinant vaccinia virus:Immunization against multiple pathogens, Science 229: 981–984

12. Evans J. D., J. McKeating, J. M. Meredith, K. L. Burke, K. Katrak,l A. John, M. Ferguson, P. D. Minor, R. A. Weiss, and J. W. Almond. 1989. An engineered Poliovirus chimaera elicits broadly reactive HIV-1 neutralizing antibodies, Nature 339: 385–388.

13. Enami M., W. Luytjes, M. Krystal, and P. Palese et al. 1990. Introduction of site-specific mutations into the genome of Influenza virus, Proc. Natl. Acad. Sci. USA 87: 3802–3805.

14. Muster T., E. K. Subbarao, M. Enami, B. R. Murphy, and P. Palese. 1991. An Influenza A virus containing Influenza B virus 5' and 3' noncoding regions on the neuraminidase gene is attenuated in mice, Proc. Natl. Acad. Sci. USA 88: 5177–5181.

15. Li, S, J. L. Schulmann, T. Moran, C. Bona, and P. Palese. 1992. Influenza-A virus transfectants with chimeric Hemagglutinins containing epitopes from different subtypes, J. Virol.66.: 399–404

16. Nisonoff A., E. Lamoyi. 1981. Clin. Immunol. Immunopathol. 21: 397

17. Sacks D. L., K. M. Esser and A. Sher. 1982. J. Exp. Med. 155: 1108

18. Kauffman R. S., J. H. Noseworthy, J. T. Nepom, R. Finberg, B. N. Fields, and M. I. Greene. 1983. J. Immunol. 131: 2539

19. Sharpe A. H., G. N. Gaulton, K. K. McDade, B. N. Fields, and M. I. Greene. 1984. J. Exp. Med. 160: 1195

20. Gaulton G. N., and M. I. Greene. 1986. Ann. Rev. Immunol. 4: 253

21. Broliden, P., A. Gegerfelt, P. Clapham, J. Rosen, E. Fenyö, B. Wahren, and K. Broliden. 1992. Identification of human neutralizing regions of the human immunodeficiency virus type-1 envelope glycoproteins, Proc. Natl. Acad. Sci. USA 89/2:461–465.

22. Teeuwsen V. J., K. H. Siebelnik, S. Crush-Stanton, A. D. B. Swerdlow, J. J. Schalken, J. Goudsmit, R. Van De Akker, M. J. Stukart, F. G. Uytdehaag, and A. D. Osterhaus. 1990. Production and characterization of a human monoclonal antibody, reactive with conserved epitope on gp41 of human immunodeficiency virus type 1, AIDS Res Hum Retroviruses 6: 381–392.

22a. Scott, J. K. and G. P. Smith. 1990, Searching for peptide ligands with an epitope library, Science 249: 386–390

23. Neurath, A. R., N. Strick, P. Taylor, P. Rubinstein, and C. E. Stevens. 1990. Search for epitipe-specific antibody responses to the human immunodeficiency virus (HIV-1) envelope glycoproteins signifying resistance to desease development, AIDS Res Hum Retroviruses 6: 1183–1191

24. Sambrook, J., E. F. Fritsch and T. Maniatis. 1989. Molecular Cloning. A Laboratory manual. Cold Spring Harbor Laboratory Press, New York 25. Wharton, S. A., W. Weis, J. J. Shekel, and D. C. Wiley. 1989. Structure, function and antigenicity of the Hemagglutinin of Influenza virus, in: R. M. Krug (ed), The Influenza Viruses, Plenum Press, New York 26. Wiley, D. C., I. A. Wilson and J. J. Shekel. 1981. Structural identification of the antibody binding sites of Hong Kong Influenza Hemagglutinin and their involvement in the antigenic variation, Nature 289: 373–378

27. Kohl, J., F. Rüker, G. Himmler, E. Razazzi, and H. Katinger. 1991. Cloning and expression of a HIV-1 specific single-chain Fv region fused to *Escherichia coli* Alkaline Phosphatase, Ann. New York Acad. Sci. 646: 106–114

We claim:

1. An isolated polynucleotide consisting of eighteen basepairs encoding a peptide consisting of six amino acids and having an amino acid sequence selected from the group consisting of SEQ. ID. NOs.:1–25, wherein said peptide induces HIV-1 neutralizing antibodies in a subject.

2. The isolated polynucleotide of claim 1, wherein the nucleotide sequence is selected from the group consisting of SEQ. ID. NOs.:26–50.

3. An isolated polynucleotide comprising a first polynucleotide consisting of eighteen basepairs encoding a peptide consisting of six amino acids and having an amino acid sequence selected from the group consisting of SEQ. ID. NOs.:1–25, wherein said peptide induces HIV-1 neutralizing antibodies in a subject and a second polynucleotide that encodes a carrier protein.

4. The isolated polynucleotide of claim 3, wherein the carrier protein is selected from the group consisting of an antibody, an antibody fragment, a phage protein, and glutathione-S-transferase.

5. The isolated polynucleotide of claim 3, wherein the carrier protein is an antigenic viral protein.

6. The isolated polynucleotide of claim 4, wherein the carrier protein is a phage protein III of the filamentous phage FUSE5 or a single chain Fv antibody fragment.

7. The isolated polynucleotide of claim 5, wherein said viral protein is a protein of a virus selected from the group consisting of vaccinia, polio Sabin type 1, influenza virus and hepatitis B.

8. The isolated polynucleotide of claim 7, wherein said protein is selected from the group consisting of a hemagglutinin of influenza virus, a neuraminidase of influenza virus, a core protein of hepatitis B virus and a surface antigen of hepatitis B virus.

9. The isolated polynucleotide of claim 5, wherein the carrier protein is hemagglutinin of influenza virus.

10. The isolated polynucleotide of claim 3, wherein the first polynucleotide sequence is linked to the 3' end of the second polynucleotide sequence.

11. The isolated polynucleotide of claim 4, wherein the first polynucleotide sequence is linked to the 3' end of the second polynucleotide sequence.

12. The isolated polynucleotide of claim 3, wherein the first polynucleotide sequence is embedded within the second polynucleotide sequence.

13. The isolated polynucleotide of claim 12, wherein the first polynucleotide sequence is embedded within a polynucleotide sequence encoding an influenza hemagglutinin protein, a phage protein III of the filamentous phage FUSE5, or the linker portion joining the variable region of the light chain to the variable region of the heavy chain of a monoclonal antibody.

14. The isolated polynucleotide of claim 1, wherein the peptide has an amino acid sequence selected from the group consisting of SEQ. ID. NOs.:10–25.

15. The isolated polynucleotide of claim 1, wherein the nucleotide sequence is selected from the group consisting of SEQ. ID. NOs.:35–50.

16. The isolated polynucleotide of claim 3, wherein the peptide has an amino acid sequence selected from the group consisting of SEQ. ID. NOs.:10–25.

17. The isolated polynucleotide of claim 4, wherein the nucleotide sequence is selected from the group consisting of SEQ. ID. NOs.:35–50.

18. The isolated polynucleotide of claim 5, wherein the nucleotide sequence is selected from the group consisting of SEQ. ID. NOs.:35–50.

* * * * *

SEQUENCE LISTING ( 1 ) GENERAL INFORMATION:

( i i i ) NUMBER OF SEQUENCES: 50

( 2 ) INFORMATION FOR SEQ ID NO: 1:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE:
( A ) DESCRIPTION: PEPTIDE ( i i i ) HYPOTHETICAL: No ( v i ) ORIGINAL SOURCE:
( A ) ORGANISM: HIV-1
( B ) STRAIN:
( C ) INDIVIDUAL ISOLATE: BH10
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 662 TO 667
( C ) IDENTIFICATION METHOD:
( D ) OTHER INFORMATION: EPITOPE OF HUMAN MONCLONAL ANTIBODY DIRECTED AGAINST HIV-1 GP160

( x i ) SEQUENCE DESCRIPTION: SEQ ID NO: 1:

Glu Leu Asp Lys Trp Ala 6
1 5

( 2 ) INFORMATION FOR SEQ ID NO: 2:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: JS4/26
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:GP160 FRAGMENT
( B ) LOCATION: RESIDUE 655 TO 660
( C ) IDENTIFICATION METHOD:
( D ) OTHER INFORMATION: EPITOPE OF A HUMAN MONOCLONAL ANTIBODY DIRECTED AGAINST HIV-1 GP160.

( x i ) SEQUENCE DESCRIPTION: SEQ ID NO: 2:

Glu Leu Asn Lys Trp Ala 6
1 5

( 2 ) INFORMATION FOR SEQ ID NO: 3:

( i ) SEQUENCE CHARACTERISTICS:
( A ) LENGTH: 6
( B ) TYPE: AMINO ACIDS
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: PATIENT 3L
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 164 TO 169
( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 3:

Glu Leu Asp Lys Trp Asp 6
1 5

( 2 ) INFORMATION FOR SEQ ID NO: 4:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: SF170
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 667 TO 672
( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 4:

Ala Leu Asp Lys Trp Ala 6
1 5

( 2 ) INFORMATION FOR SEQ ID NO: 5:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: JH3
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 673 TO 678
( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 5:

Gly Leu Asp Lys Trp Ala 6
1 5

( 2 ) INFORMATION FOR SEQ ID NO: 6:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: Z-84
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 669 TO 674
( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 6:

Gln Leu Asp Lys Trp Ala 6
1 6

( 2 ) INFORMATION FOR SEQ ID NO: 7:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:

( C ) INDIVIDUAL ISOLATE: CAM1 PROVIRAL GENOME
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 662 TO 667
( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 7:

Glu Leu Asp Thr Trp Ala 6
1 5

( 2 ) INFORMATION FOR SEQ ID NO: 8:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: JS4/6
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 659 TO 664
( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 8:

Ala Leu Asp Thr Trp Ala 6
1 5

( 2 ) INFORMATION FOR SEQ ID NO: 9:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: SBB
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

(ix) FEATURE:
(A) NAME/KEY: GP160 FRAGMENT
(B) LOCATION: RESIDUE 413 TO 418
(C) IDENTIFICATION METHOD:
(D) OTHER INFORMATION: EPITOPE OF A HUMAN MONOCLONAL ANTIBODY DIRECTED AGAINST HIV-1 GP160

(xi) SEQUENCE DESCRIPTION: SEQ ID NO: 9:

Lys Leu Asp Glu Trp Ala 6
1 5

(2) INFORMATION FOR SEQ ID NO: 10:

(i) SEQUENCE CHARACTERISTICS:
(A) LENGTH: 6
(B) TYPE: AMINO ACID
(C) STRANDEDNESS: SINGLE
(D) TOPOLOGY: UNKNOWN (ii) MOLECULE TYPE: PEPTIDE (iii) HYPOTHETICAL: No (iv) ORIGINAL SOURCE:
(A) ORGANISM: FILAMENTOUS PHAGE fUSE5
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: p3 FUSION PROTEIN FRAGMENT
(B) LOCATION: RESIDUE 4 TO 9
(C) IDENTIFICATION METHOD:
(D) OTHER INFORMATION: HEXAPEPTIDE FROM A RANDOM LIBRARY SCREENING AND ITS BINDING TO MONCLONAL ANTIBODY 2F5

(xi) SEQUENCE DESCRIPTION: SEQ ID NO: 10:

Ser Leu Asp Lys Trp Ala 6
1 5

(2) INFORMATION FOR SEQ ID NO: 11:

(i) SEQUENCE CHARACTERISTICS:
(A) LENGTH: 6
(B) TYPE: AMINO ACID
(C) STRANDEDNESS: SINGLE
(D) TOPOLOGY: Unknown (ii) MOLECULE TYPE: PEPTIDE (iii) HYPOTHETICAL: No (iv) ORIGINAL SOURCE:
(A) ORGANISM: FILAMENTOUS PHAGE fUSE5
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: p3 FUSION PROTEIN FRAGMENT
(B) LOCATION: RESIDUE 4 TO 9
(C) IDENTIFICATION METHOD:
(D) OTHER INFORMATION: HEXAPEPTIDE FROM A RANDOM LIBRARY SCREENING AND ITS BINDING TO MONCLONAL ANTIBODY 2F5

(xi) SEQUENCE DESCRIPTION: SEQ ID NO: 11:

Gly Arg Asp Lys Trp Ala 6
1 5

(2) INFORMATION FOR SEQ ID NO: 12:

(i) SEQUENCE CHARACTERISTICS:
(A) LENGTH: 6
(B) TYPE: AMINO ACID
(C) STRANDEDNESS: SINGLE
(D) TOPOLOGY: Unknown (ii) MOLECULE TYPE: PEPTIDE (iii) HYPOTHETICAL: No (iv) ORIGINAL SOURCE:
(A) ORGANISM: FILAMENTOUS PHAGE fUSE5
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: p3 FUSION PROTEIN FRAGMENT
(B) LOCATION: RESIDUE 4 TO 9
(C) IDENTIFICATION METHOD:
(D) OTHER INFORMATION: HEXAPEPTIDE FROM A RANDOM LIBRARY SCREENING AND ITS BINDING TO MONCLONAL ANTIBODY 2F5

(xi) SEQUENCE DESCRIPTION: SEQ ID NO: 12:

Gly Ala Asp Lys Trp Ala 6
1 5

(2) INFORMATION FOR SEQ ID NO: 13:

(i) SEQUENCE CHARACTERISTICS:
(A) LENGTH: 6
(B) TYPE: AMINO ACID
(C) STRANDEDNESS: SINGLE
(D) TOPOLOGY: Unknown (ii) MOLECULE TYPE: PEPTIDE (iii) HYPOTHETICAL: No (iv) ORIGINAL SOURCE:
(A) ORGANISM: FILAMENTOUS PHAGE fUSE5
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: p3 FUSION PROTEIN FRAGMENT
(B) LOCATION: RESIDUE 4 TO 9
(C) IDENTIFICATION METHOD:
(D) OTHER INFORMATION: HEXAPEPTIDE FROM A RANDOM LIBRARY SCREENING AND ITS BINDING TO MONCLONAL ANTIBODY 2F5

(xi) SEQUENCE DESCRIPTION: SEQ ID NO: 13:

Ala His Glu Lys Trp Ala 6
1 5

(2) INFORMATION FOR SEQ ID NO: 14:

(i) SEQUENCE CHARACTERISTICS:

-continued ( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 14:

Ala Cys Asp Gln Trp Ala 6
1 5

( 2 ) INFORMATION FOR SEQ ID NO: 15:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 15:

Gly Ala Asp Lys Trp Gly 6
1 5

( 2 ) INFORMATION FOR SEQ ID NO: 16:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No -continued ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 16:

Gly Ala Asp Lys Trp Asn 6
1 5

( 2 ) INFORMATION FOR SEQ ID NO: 17:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 17:

Gly Ala Asp Lys Trp Cys 6
1 5

( 2 ) INFORMATION FOR SEQ ID NO: 18:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:

(G) CELL TYPE:
(H) CELL LINE:
(I) ORGANELLE:

(ix) FEATURE:
(A) NAME/KEY: p3 FUSION PROTEIN FRAGMENT
(B) LOCATION: RESIDUE 4 TO 9
(C) IDENTIFICATION METHOD:
(D) OTHER INFORMATION: HEXAPEPTIDE FROM A RANDOM LIBRARY SCREENING AND ITS BINDING TO MONCLONAL ANTIBODY 2F5

(xi) SEQUENCE DESCRIPTION: SEQ ID NO: 18:

Gly Ala Asp Lys Trp Val 6
1 5

(2) INFORMATION FOR SEQ ID NO: 19:

(i) SEQUENCE CHARACTERISTICS:
(A) LENGTH: 6
(B) TYPE: AMINO ACID
(C) STRANDEDNESS: SINGLE
(D) TOPOLOGY: Unknown (ii) MOLECULE TYPE: PEPTIDE (iii) HYPOTHETICAL: No (iv) ORIGINAL SOURCE:
(A) ORGANISM: FILAMENTOUS PHAGE fUSE5
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: p3 FUSION PROTEIN FRAGMENT
(B) LOCATION: RESIDUE 4 TO 9
(C) IDENTIFICATION METHOD:
(D) OTHER INFORMATION: HEXAPEPTIDE FROM A RANDOM LIBRARY SCREENING AND ITS BINDING TO MONCLONAL ANTIBODY 2F5

(xi) SEQUENCE DESCRIPTION: SEQ ID NO: 19:

Gly Ala Asp Lys Trp His 6
1 5

(2) INFORMATION FOR SEQ ID NO: 20:

(i) SEQUENCE CHARACTERISTICS:
(A) LENGTH: 6
(B) TYPE: AMINO ACID
(C) STRANDEDNESS: SINGLE
(D) TOPOLOGY: Unknown (ii) MOLECULE TYPE: PEPTIDE (iii) HYPOTHETICAL: No (iv) ORIGINAL SOURCE:
(A) ORGANISM: FILAMENTOUS PHAGE fUSE5
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: p3 FUSION PROTEIN FRAGMENT
(B) LOCATION: RESIDUE 4 TO 9
(C) IDENTIFICATION METHOD:

( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 20:

Gly Ala Asp Lys Cys His 6
1 5

( 2 ) INFORMATION FOR SEQ ID NO: 21:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 21:

Gly Ala Asp Lys Cys Gln 6
1 5

( 2 ) INFORMATION FOR SEQ ID NO: 22:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 22:

Ala Tyr Asp Lys Trp Ser 6
1 5

( 2 ) INFORMATION FOR SEQ ID NO: 23:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 23:

Ala Phe Asp Lys Trp Val 6
1 5

( 2 ) INFORMATION FOR SEQ ID NO: 24:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 24:

Gly Pro Asp Lys Trp Gly 6
1 5

( 2 ) INFORMATION FOR SEQ ID NO: 25:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 25:

Ala Arg Asp Lys Trp Ala 6
1 5

( 2 ) INFORMATION FOR SEQ ID NO: 26:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: BH10
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 26:

GAATTAGATA AATGGGCA 18

( 2 ) INFORMATION FOR SEQ ID NO: 27:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: JS4/26
( D ) DEVELOPMENTAL STAGE:

( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 27:

GAATTGAATA AGTGGGCA 18

( 2 ) INFORMATION FOR SEQ ID NO: 28:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: PATIENT 3L
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 28:

GAATTAGATA AGTGGGAC 18

( 2 ) INFORMATION FOR SEQ ID NO: 29:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: SF170
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

-continued ( x i ) SEQUENCE DESCRIPTION: SEQ ID NO: 29:

GCATTGGACA AGTGGGCA 18

( 2 ) INFORMATION FOR SEQ ID NO: 30:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: JH3
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 30:

GGGTTAGATA AATGGGCA 18

( 2 ) INFORMATION FOR SEQ ID NO: 31:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: Z-84
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 31:

CAATTGGACA AATGGGCA 18

( 2 ) INFORMATION FOR SEQ ID NO: 32:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE:CAM1 PROVIRAL GENOME
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 32:

GAATTGGATA CGTGGGCA 18

( 2 ) INFORMATION FOR SEQ ID NO: 33:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: JS4/6
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 33:

GCATTGGATA CGTGGGCA 18

( 2 ) INFORMATION FOR SEQ ID NO: 34:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: SBB
( D ) DEVELOPMENTAL STAGE:
( E ) HAPLOTYPE:
( F ) TISSUE TYPE:

( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 34:

AAGTTAGATG AGTGGGCA 18

( 2 ) INFORMATION FOR SEQ ID NO: 35:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION: RESIDUES 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 35:

TCGCTTGATA AGTGGGCC 18

( 2 ) INFORMATION FOR SEQ ID NO: 36:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION: RESIDUES 10-27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 36:

GGGCGTGATA AGTGGGCG 18

( 2 ) INFORMATION FOR SEQ ID NO: 37:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 37:

GGGGCTGATA AGTGGGCG 18

( 2 ) INFORMATION FOR SEQ ID NO: 38:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 38:

GCTCATGAAA AGTGGGCG 18

( 2 ) INFORMATION FOR SEQ ID NO: 39:

( i ) SEQUENCE CHARACTERISTICS:
( A ) LENGTH: 18
( B ) TYPE: NUCLEIC ACID ( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 39:

G C T T G T G A T C A G T G G G C G 1 8

( 2 ) INFORMATION FOR SEQ ID NO: 40:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN
( B ) LOCATION: RESIDUES 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 40:

G G A G C T G A T A A G T G G G G T 1 8

( 2 ) INFORMATION FOR SEQ ID NO: 41:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:

-continued ( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 41:

G G A G C T G A T A A G T G G A A T 1 8

( 2 ) INFORMATION FOR SEQ ID NO: 42:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 42:

G G C G C T G A T A A A T G G T G T 1 8

( 2 ) INFORMATION FOR SEQ ID NO: 43:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE

-continued ( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 43:

GGCGCTGATA AATGGGTT 18

( 2 ) INFORMATION FOR SEQ ID NO: 44:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 44:

GGGGCTGATA AGTGGCAT 18

( 2 ) INFORMATION FOR SEQ ID NO: 45:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 45:

GGAGCTGATA AATGTCAT 18

( 2 ) INFORMATION FOR SEQ ID NO: 46:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 46:

G G A G C T G A T A A A T G T C A G 1 8

( 2 ) INFORMATION FOR SEQ ID NO: 47:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 47:

G C T T A T G A T A A G T G G A G T 1 8

( 2 ) INFORMATION FOR SEQ ID NO: 48:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 48:

G C T T T T G A T A   A G T G G G T T   1 8

( 2 ) INFORMATION FOR SEQ ID NO: 49:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 49:

G G G C C T G A T A   A A T G G G G T   1 8

( 2 ) INFORMATION FOR SEQ ID NO: 50:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:

-continued ( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 50:

GCTCGTGATA AGTGGGCG 18